United States Patent [19]

Nishimura et al.

[11] Patent Number: 5,491,171
[45] Date of Patent: Feb. 13, 1996

[54] PHARMACEUTICAL PREPARATION CONTAINING PROSTAGLANDIN COMPOUND FOR RECTAL OR VAGINAL ADMINISTRATION

[75] Inventors: Ken-ichi Nishimura, Kyoto; Akihisa Yoshimi, Osaka; Takayoshi Mori, Kyoto; Nobuharu Kakeya, Nagaokakyo; Masahiro Kikuchi, Osaka; Nobuo Kondoh, Osaka; Takeshi Uchida, Osaka; Koichi Yamanouchi, Osaka, all of Japan

[73] Assignees: Kyoto Pharmaceutical Industries, Ltd., Kyoto; The Green Cross Corporation, Osaka, both of Japan

[21] Appl. No.: 232,255

[22] PCT Filed: Nov. 5, 1992

[86] PCT No.: PCT/JP92/01431

§ 371 Date: Jul. 27, 1994

§ 102(e) Date: Jul. 27, 1994

[87] PCT Pub. No.: WO93/08804

PCT Pub. Date: May 13, 1993

[30] Foreign Application Priority Data

Nov. 8, 1991 [JP] Japan ................................. 3-321254

[51] Int. Cl.⁶ .......................... A61K 31/20; A61K 31/19; A61K 31/557
[52] U.S. Cl. ..................... 514/558; 514/560; 514/573; 514/966; 514/967

[58] Field of Search ....................... 514/558, 560, 514/573, 966, 967

[56] References Cited

U.S. PATENT DOCUMENTS

| | | | |
|---|---|---|---|
| 4,289,785 | 9/1981 | Wilks | 424/279 |
| 4,352,790 | 10/1982 | Johansson et al. | 424/78 |
| 4,485,033 | 11/1984 | Kitao et al. | 252/315.4 |

FOREIGN PATENT DOCUMENTS 0056065  7/1982  European Pat. Off. .

OTHER PUBLICATIONS

*Chemical Abstracts*, vol. 112, No. 4, 22 Jan. 1990, Abstract No. 25693.

Primary Examiner—Kimberly Jordan
Attorney, Agent, or Firm—Sughrue, Mion, Zinn, Macpeak & Seas

[57] ABSTRACT

A pharmaceutical preparation for rectal or vaginal administration, comprising a prostaglandin compound and an alkali metal salt of a fatty acid having 8 to 12 carbon atoms, and a method for administering a prostaglandin compound, comprising rectally or vaginally administering same in the presence of an alkali metal salt of a fatty acid.

According to the present invention, absorption of prostaglandin from rectum or vagina can be enhanced.

The prostaglandin can be stabilized in the preparation.

5 Claims, No Drawings

PHARMACEUTICAL PREPARATION CONTAINING PROSTAGLANDIN COMPOUND FOR RECTAL OR VAGINAL ADMINISTRATION

This application is a 371 of Pat./JP92/01431 filed Nov. 5, 1992.

TECHNICAL FIELD

The present invention relates to a pharmaceutical preparation for rectal or vaginal administration, which contains a pharmaceutically useful prostaglandin compound (hereinafter referred to as PG). The pharmaceutical preparation allows superior absorption of PG.

BACKGROUND ART

PG is a group of physiologically active substances synthesized in animal tissues from eicosapolyenoic acid such as arachidonic acid. Said compound is known to show a wide range of pharmacological actions such as hypotensive action, platelet aggregation-inhibitory action, vasodilating action, blood flow increasing action, gastric juice secretion-suppressing action, intestine hyperkinetic action, oxytocic action, diuretic action, bronchodilating action, contracting action and so on.

PG is hardly absorbed by oral administration and therefore generally administered by injection. Injections, however, give pain to patients.

Injections, moreover, require patients to go to the doctor by themselves, giving burdens on the patients in terms of time and physical labor, and development and practical application of a dosage form other than injection have been desired. In doing so, it is essential to solve technical problems with regard to achieving high bioavailability of a slightly-absorbable drug and the stabilization of unstable PG.

The present invention aims at solving the above-mentioned problems. That is, the present invention aims at solving the above problems by providing PG, which has been conventionally administered as injections, in other dosage forms and employing other administration method.

DISCLOSURE OF THE INVENTION

In order to solve the aforementioned problems, the present inventors have studied the relations between the dosage form of PG, administration route etc. and bioavailability and found that rectal or vaginal administration of PG surprisingly results in effective absorption of PG from these mucosal layers and exertion of the desired pharmacological effects; that presence of an alkali metal salt of a fatty acid having 8 to 12 carbon atoms therealong results in easy absorption of PG from rectum or vagina and migration thereof into blood; and that the use of an oily base as a base for a pharmaceutical preparation and the presence of an alkali metal salt of a fatty acid having 8 to 12 carbon atoms result in stabilization of PG and easy absorption of PG from rectum or vagina, based on which findings the present invention has been completed.

There has been no report on a pharmaceutical preparation of PG for rectal or vaginal administration, or its bioavailability. In addition, it is not possible to easily predict what pharmaceutical agent shows high bioavailability by rectal or vaginal administration.

The present invention is as follows:

(1) A PG-containing pharmaceutical preparation for rectal or vaginal administration, containing PG and an alkali metal salt of a fatty acid having 8 to 12 carbon atoms.

(2) A method for administering PG by rectal or vaginal administration of PG in the presence of an alkali metal salt of a fatty acid having 8 to 12 carbon atoms.

The present invention is explained in detail in the following.

The PG per se which is an active ingredient in the present invention is a compound substantially known and having a prostanic acid as a basic structure, and classified into respective groups of A through I according to the presence of oxygen atom bonded to a 5-membered ring and a double bond therein. In the present invention, various types of prostaglandin and derivatives thereof which are generally called prostaglandin are all encompassed. For example, the derivatives thereof include a 7-thia compound, a 9-acyloxy compound, an alkyl ester compound, an alkoxycarbonylalkyl ester compound, an acyloxycarbonylalkyl ester compound and so on with diverse pharmacological activities as mentioned above.

The dose of PG in the pharmaceutical preparation of the invention is 1–10,000 μg per administration to an adult. According to the present invention, a significant effect and sufficient duration of the effect are evidently achieved by administering PG via rectum or vagina.

The alkali metal salt of a fatty acid having 8 to 12 carbon atoms to be used in the present invention is preferably straight chain and exemplified by sodium salt or potassium salt of, for example, capric acid, lauric acid, caprylic acid or pelargonic acid. The salt of a fatty acid is generally used in the preparation in a proportion of 0.5–20% by weight, preferably 1–5% by weight. It is used generally in a proportion of 45–36,000,000 parts by weight, preferably 90–9,000,000 parts by weight relative to 100 parts by weight of PG.

Examples of the dosage form of the preparation of the present invention include, in addition to the conventional rectal suppositories and vaginal suppositories, soft capsules containing a liquid oily base or ointment and tubes containing same for injection when in use. As the base, exemplified are oily base, water-soluble base, emulsion base, ointment-like base and so on. For example, the oily base includes fats and oils such as peanut oil, olive oil, corn oil, castor oil, cacao butter, laurin fat, glycerol fatty acid ester, specifically Pharmasol (product of NOF Corp.), Witepsol (product of Dinamite Nobel Inc.), SB-base (product of Kaneka Corp.) and lanolin fat. Examples of the water-soluble base include polyethylene glycol, polypropylene glycol, glycerin and glycerogelatin. The base emulsion is an emulsified base of water-soluble base and oily base and may be of an O/W type or W/O type. In the present invention, an oily base is preferably used, by which PG is highly stabilized and superior pharmacological effects of PG can be achieved. These bases may be used solely or in an appropriate combination.

It has been found in the present invention, in particular, that the use of an oily base as a base and the aforementioned alkali metal salt of a fatty acid as an absorption enhancer can bring about the most preferable bioavailability of PG. The most desirable embodiment of the present invention is a rectal or vaginal suppository combining the both agents mentioned above.

The preparation of the present invention is easily prepared according to a general production method known per se.

The present invention is described in detail by the illustration of examples. The present invention is not limited to the scope shown by the following examples.

Example 1

Pharmasol B-105 (8.80 g, produced by NOF Corp.) was dissolved well at not more than 40° C. Thereto was added sodium caprate (0.18 g) passed through a 100-mesh sieve and the mixture was thoroughly stirred to disperse them homogeneously. Then, $PGE_1$ (0.02 g) passed through a 100-mesh sieve was added thereto and homogeneously dispersed therein. The mixture was filled in a container for suppository by 0.9 g to give a rectal suppository or vaginal suppository.

Example 2

A suppository (rectal or vaginal suppository) having the following formulation was prepared by a conventional method.

| | |
|---|---|
| $PGE_1$ | 2 mg |
| sodium caprate | 18 mg |
| emulsion base | 880 mg |
|   Pharmasol B-115 | 150 mg |
|   PEG 1000 | 450 mg |
|   Unilube 70DP-950B | 110 mg |
|   Panacet 810 | 170 mg |
| Total | 900 mg |

Experiment 1

A dog fasted for 16 hours was anesthetized by an intravenous administration of sodium pentobarbital (25 mg/kg body weight) and fixed at a dorsal position. The right common carotid artery was dissected from surrounding tissue and attached with a flow probe which was connected to an electromagnetic flowmeter. The suppositories shown in Table 1 were administered and common carotid artery flow was measured with time. The results are shown in Table 1. The composition of each suppository used in the experiment is as shown in Table 2.

TABLE 1

| | | | $PGE_1$ suppository with a base of oil or fat | | | | |
|---|---|---|---|---|---|---|---|
| | | | Common carotid artery blood flow (%)[#] | | | | |
| Suppository | $PGE_1$ amount μg | Sodium caprate content | Before administration | After administration | | | |
| | | | | 10 min | 30 min | 60 min | 120 min |
| 1 | 0 | 0% | 100 ± 0 | 104 ± 2 | 111 ± 5 | 109 ± 7 | N.T. |
| 2 | 0 | 2% | 100 ± 0 | 102 ± 5 | 103 ± 12 | 111 ± 11 | N.T. |
| 3 | 2000 | 0% | 100 ± 0 | 113 ± 11 | 117 ± 4* | 109 ± 4 | 95 ± 6 |
| 4 | 2000 | 2% | 100 ± 0 | 129 ± 4*** | 123 ± 9 | 121 ± 5* | 112 ± 13 |

Note
[#]Percent relative to the value before administration, Mean ± S.E. (n = 3)
*$p < 0.05$
**$p < 0.01$
***$p < 0.01$ (against value before administration)

TABLE 2

| | | Suppository 1 | Suppository 2 | Suppository 3 | Suppository 4 |
|---|---|---|---|---|---|
| $PGE_1$ | (mg) | — | — | 2 | 2 |
| Sodium caprate | (mg) | — | 18 | — | 18 |
| Pharmasol B-105 | (mg) | 900 | 882 | 898 | 880 |
| Total | (mg) | 900 | 900 | 900 | 900 |

Experiment 2

A suppository having the following formulation A (without sodium caprate) or B (with 2 W/W % sodium caprate) was preserved at 5° C. for 18 months and the residual content of $PGE_1$ was measured, the results of which are shown in Table 3.

TABLE 3

| | Indicated amount of $PGE_1$ | Residual content after preservation (%) |
|---|---|---|
| Formulation A | 50 μg | 54.8 |
| Formulation B | 50 μg | 98.5 |

| Formulation A: | $PGE_1$ | 50 μg |
|---|---|---|
| | Pharmasol B-105 | 899.95 mg |
| | Total | 900 mg |
| Formulation B: | $PGE_1$ | 50 μg |
| | Sodium caprate | 18 mg |
| | Pharmasol B-105 | 881.95 mg |
| | Total | 900 mg |

According to the present invention, the PG conventionally administered by injection can be administered via rectum or vagina, removing the inconveniences, pain, physical burden etc. caused by the conventional administration by injection. Furthermore, the preparation of the present invention permits a sustained pharmacological action over an extended period of time and is conducive to a good bioavailability.

We claim:

1. A pharmaceutical preparation for rectal or vaginal administration, comprising a pharmaceutically useful amount of a prostaglandin compound and an alkali metal salt of capric acid, said compound and salt being dispersed in an oily base.

2. The preparation of claim 1, wherein the alkali metal salt of capric acid is a sodium salt of capric acid.

3. The preparation of claim 1, comprising the alkali metal salt of capric acid in a proportion of 0.5–20% by weight in the preparation.

4. The preparation of claim 1, which is a suppository.

5. A method for administering prostaglandin, comprising rectally or vaginally administering the pharmaceutical preparation of claim 1.

* * * * *